(12) United States Patent
Burgoon et al.

(10) Patent No.: US 10,221,906 B2
(45) Date of Patent: **\*Mar. 5, 2019**

(54) FLOATING ROTOR DISC/HUB WITH RETENTION RING FASTENER

(71) Applicant: Performance Friction Corporation, Clover, SC (US)

(72) Inventors: Donald L. Burgoon, Charlotte, NC (US); Konan Perez, Lake Wylie, SC (US); Mark Wagner, Weddington, NC (US)

(73) Assignee: PERFORMANCE FRICTION CORPORATION, Clover, SC (US)

( \* ) Notice: Subject to any disclaimer, the term of this patent is extended or adjusted under 35 U.S.C. 154(b) by 0 days.

This patent is subject to a terminal disclaimer.

(21) Appl. No.: 15/268,343

(22) Filed: Sep. 16, 2016

(65) Prior Publication Data

US 2017/0002878 A1  Jan. 5, 2017

Related U.S. Application Data

(60) Provisional application No. 62/219,597, filed on Sep. 16, 2015.

(51) Int. Cl.
| | |
|---|---|
| *F16D 65/12* | (2006.01) |
| *A61F 9/02* | (2006.01) |
| *A61F 11/12* | (2006.01) |
| *A61F 11/08* | (2006.01) |
| *F16D 65/02* | (2006.01) |

(52) U.S. Cl.
CPC ............ *F16D 65/123* (2013.01); *A61F 9/029* (2013.01); *A61F 11/08* (2013.01); *A61F 11/12* (2013.01); *F16D 2065/1316* (2013.01); *F16D 2065/1356* (2013.01)

(58) Field of Classification Search
CPC .......... F16D 65/123; F16D 2065/1316; F16D 2065/1364
See application file for complete search history.

(56) References Cited

U.S. PATENT DOCUMENTS 3,313,385 A     4/1967 Forster
3,542,166 A  \* 11/1970 Harrison ............... F16D 65/123
                                                                188/218 XL
(Continued)

FOREIGN PATENT DOCUMENTS

DE        10125115 A1 \* 12/2002 ......... F16D 65/0006
DE        10358088 A1    7/2005
(Continued)

OTHER PUBLICATIONS

Machine translation of DE 10125115 (no date).\*
(Continued)

*Primary Examiner* — Nicholas J Lane
(74) *Attorney, Agent, or Firm* — Roberts Mlotkowski Safran Cole & Calderon, P.C.

(57) ABSTRACT

A floating disc brake assembly having a disc brake rotor secured to a hub with a retention ring structured and arranged to fit within retention ring flanges of a plurality of rotor mounting tabs extending from the hub. A method of uniformly transferring braking forces from a rotor of a brake assembly about a hub of the brake assembly and a kit of parts are also provided.

14 Claims, 12 Drawing Sheets

(56) References Cited

U.S. PATENT DOCUMENTS

| | | |
|---|---|---|
| 5,826,684 A | 10/1998 | Hester |
| 5,988,613 A | 11/1999 | Dagh et al. |
| 6,135,247 A | 10/2000 | Bodin et al. |
| 6,336,531 B1 | 1/2002 | Chou |
| 6,467,588 B1 | 10/2002 | Baumgartner et al. |
| 6,564,913 B2 | 5/2003 | Baumgartner et al. |
| 6,626,273 B1 | 9/2003 | Baumgartner et al. |
| 6,910,556 B1 | 6/2005 | Baumgartner et al. |
| 7,410,036 B2 | 8/2008 | Wimmer et al. |
| 7,607,377 B1 | 10/2009 | Greenwald |
| 7,665,584 B2 | 2/2010 | Hirotomi et al. |
| 7,918,322 B2 | 4/2011 | Pahle |
| 7,934,777 B1 | 5/2011 | Yuhas |
| 8,256,599 B2 | 9/2012 | Goto et al. |
| 8,342,298 B2 | 1/2013 | Ilg et al. |
| 8,454,290 B2 | 6/2013 | Schaser et al. |
| 8,651,247 B2 | 2/2014 | Burgoon et al. |
| 8,651,249 B2 | 2/2014 | Lee |
| 9,249,848 B2 | 2/2016 | Kokott |
| 9,657,794 B2 | 5/2017 | Morio et al. |
| 9,709,108 B2 | 7/2017 | Wurth et al. |
| 9,714,685 B2 | 7/2017 | Root |
| 9,759,281 B1 | 9/2017 | Stratton et al. |
| 2004/0178030 A1 | 9/2004 | Pacchiana et al. |
| 2004/0182660 A1 | 9/2004 | Cavagna et al. |
| 2005/0145452 A1* | 7/2005 | Yamamoto ............... F16D 65/12 188/218 XL |
| 2007/0029146 A1 | 2/2007 | Huang |
| 2007/0193837 A1 | 8/2007 | Lamb |
| 2008/0099288 A1 | 5/2008 | Burgoon et al. |
| 2009/0078515 A1 | 3/2009 | Xia |
| 2011/0031332 A1 | 2/2011 | Sesser et al. |
| 2012/0067679 A1 | 3/2012 | Lee |
| 2012/0097491 A1 | 4/2012 | Yamanaka et al. |
| 2012/0247883 A1 | 4/2012 | Root |
| 2014/0151166 A1 | 6/2014 | Tironi et al. |
| 2015/0015057 A1 | 1/2015 | Oberti et al. |
| 2015/0034430 A1 | 2/2015 | Nakamura |
| 2015/0096850 A1 | 4/2015 | Hanna et al. |
| 2016/0160948 A1 | 6/2016 | Wagner et al. |
| 2016/0258500 A1 | 9/2016 | Sabeti |
| 2016/0298706 A1* | 10/2016 | Rau, III ................ F16D 65/123 |
| 2017/0074336 A1* | 3/2017 | Burgoon ............... F16D 65/123 |
| 2017/0074337 A1* | 3/2017 | Borner ................. F16D 65/123 |

FOREIGN PATENT DOCUMENTS

| | | | |
|---|---|---|---|
| DE | 102007035512 A1 | 1/2009 | |
| DE | 102008019263 A1 | 10/2009 | |
| DE | 102011053383 A1 | 3/2012 | |
| DE | 102012003159 A1 * | 8/2013 | ............ F16D 65/12 |
| DE | 102012010875 A1 | 12/2013 | |
| EP | 1553322 A1 | 7/2005 | |
| EP | 2025965 A1 | 2/2009 | |
| WO | 2006/047887 A1 | 5/2006 | |
| WO | WO 2006047887 A1 * | 5/2006 | ............ F16D 65/12 |
| WO | 2009/015740 A1 | 2/2009 | |

OTHER PUBLICATIONS

English-language abstract for DE 102012003159 (no date).*
International Search Report and Written Opinion; PCT/US2016/052334 dated Dec. 12, 2016.
International Search Report and Written Opinion; PCT/US2016/052330 dated Dec. 14, 2016.
International Search Report and Written Opinion; PCT/US2016/052287 dated Dec. 9, 2016.

* cited by examiner

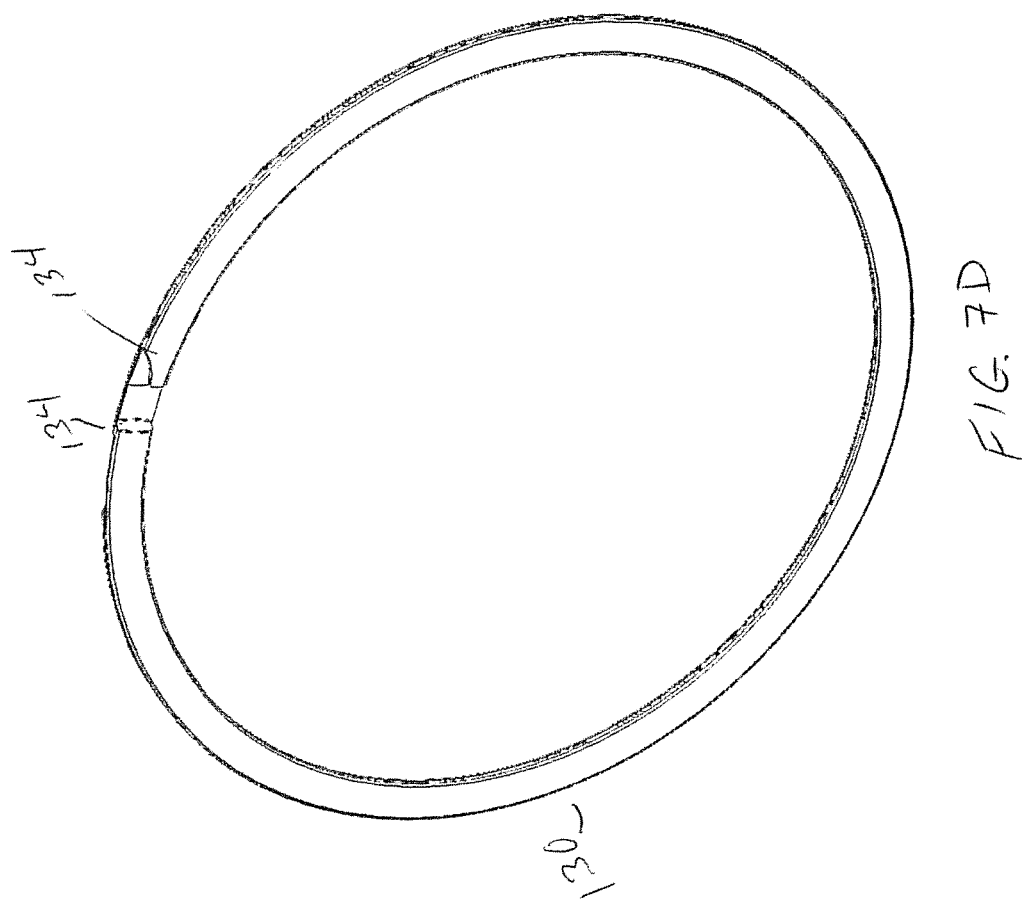

FLOATING ROTOR DISC/HUB WITH RETENTION RING FASTENER

RELATED APPLICATION

This application claims priority under 35 U.S.C. § 119(e) to U.S. Provisional Application No. 62/219,597, filed on Sep. 16, 2015, which is incorporated herein by reference in its entirety.

FIELD

This disclosure relates to improvements in vehicular disc brake assemblies.

BACKGROUND

One type of common prior art brake design for vehicles is a two piece rotor and hub in which a rotor that carries the braking surface is detachably connected to a wheel hub. Another common type of brake design is an integrated one-piece rotor and hub assembly.

Integrated one-piece rotor and hub assemblies have the advantage that no fasteners are required between the rotor and the hub. As a result, the integrated assemblies do not face problems associated with fasteners such as wear and fatigue near fastener openings and potential misalignment due to imperfect machining. A significant drawback, however, is that the assembly is constrained at the hub, which causes thermal distortion of the rotor. During braking, the rotor in such an assembly is subjected to high frictional forces that generate heat in the rotor causing thermal expansion/distortion, temperature variation across the face of the rotor, and heat transfer to the adjacent components including the hub and the bearings. Thermal expansion of the rotor is very limited because of the integral connection between the rotor and the hub, which results in thermal coning of the rotor surface and a large thermal gradient, which will induce high thermal stress leading to thermal cracking. The high thermal gradient generated during braking and the effects of the thermal expansion and distortion can cause vibration and thermal judder across the brake surfaces, resulting in rough or irregular braking pulsations, reduce the life and performance of the rotor and increase maintenance costs. Such thermal distortion can damage the rotor and when the rotor is damaged or worn, the entire integrated assembly must be replaced. This is expensive and time consuming.

One way the thermal stresses have been addressed is to provide a "floating" rotor in which the fastener connection between the rotor and the hub is provided with a small clearance or float that allows thermal expansion. Advantageously, in these designs the rotor is mounted directly to the hub such that braking force is applied in-plane to the hub thus minimizing torsion or twist between the rotor and hub attachment, which can result in cracking and breaking of the rotor or hub.

Two-piece rotor/hub assemblies also allow greater flexibility with respect to use with different hubs, as the same rotor disc can be used with different hubs. This reduces the cost since generic rotor discs can be used and only the hub portion requires specialized casting, tooling and machining steps. Thus, floating rotor/hub assemblies reduce the necessity for complete replacement of a worn, cracked or distorted rotor, since the rotor disc can be detached from the hub for less expensive and easier replacement than with the integrated design. Other advantages of integrating the rotor mount with the hub is reduced weight as compared to rotor/hat designs, wherein the hat portion is usually made of iron for OEM vehicles, and the ease of assembly or replacing parts in the field.

However, stresses induced by conventional fastener assemblies in these designs are also a problem, even in floating rotor brakes. In most conventional designs a rotor attachment flange is held against the hub with a series of bolts or studs capped with nuts at a central portion of the rotor. The hub portion is placed on one side of the attachment flange and a fastener connects the hub portion to the side of the attachment flange. During braking, a frictional force is applied to the rotor surface, which creates torque that is transferred to the attachment flange, to the fastener, through the hub. Because the hub portion is attached to one side of the attachment flange, which is in a plane axially displaced from the friction braking surface, a moment arm is created at this connection joint. When the torque is transferred through a moment arm, bending stresses are formed in the connection. This creates twisting in the areas adjacent the fastener, which can create fatigue leading to cracking and breaking. These bolts or studs absorb and transfer a major amount of the braking force to the hub and are thus subject to intense thermal and bending stresses during braking.

Torque transfer also tends to be non-uniform through the perforated flange, especially in a floating design, as the machining tolerance at each aperture causes certain connections to receive more torque than other connections. This creates high stresses at individual apertures and can cause the attachment flange to crack or to have portions break off.

The two-piece hub/rotor assemblies discussed above also have drawbacks associated with the hub portion, which typically has slots that match with the perforations in the rotor attachment flange. Some floating type two piece hub/rotor assemblies use a spacer, sometimes called a bobbin, to provide the clearance that accommodates thermal expansion. The bobbin fits in the slots of the hub piece or in slots of the rotor flange, and when torque is applied to the hub through the rotor, the bobbin twists in the slot. This twisting causes the edges of the bobbin, which are typically square to match the slot, to gouge the sides of the slots, thus damaging the slotted piece. This is especially true when the hub piece is manufactured from a material having a lower hardness, such as aluminum, which is popular in high performance and racing applications, or when the rotor is formed of cast iron.

As such, these parts represent another weak link in the system, and can break-off during maintenance procedures. Additionally, holes drilled in the rotors for receiving these connectors can weaken the overall design and likewise crack due to the thermal and torsional forces created during braking.

However, despite recent advances, there remains an unmet need in the art to optimize and simplify attachment of floating disc brake rotors to wheel hubs.

There is a need, therefore, to provide a hub and rotor assembly that eliminates bending stresses and promotes uniform torque transfer, so as to minimize bending and fatigue stresses to increase the life and reliability of the brake device.

SUMMARY

Presented is a floating disc brake assembly, comprising a disc brake rotor comprising an inner circumferential aperture having a plurality of rotor tabs spaced about the aperture; a hub comprising a cylindrical axial body having axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, the slots structured and arranged for receiving the rotor tabs; and at least one retention ring for securing the rotor tabs between the rotor mounting tabs and the rotor mounting flange, the retention ring structured and arranged to fit within the retention ring flanges of the plurality of rotor mounting tabs.

Additionally, the floating disc brake assembly further comprises landings extending across at least some of the slots between the rotor mounting tabs, such that when engaged with the retention ring flanges, the retention ring and the landings axially retain the rotor tabs in the slots.

In another form, the rotor tabs and the rotor mounting tabs are substantially coplanar when the rotor is mounted on the hub.

Advantageously, neither the rotor tabs nor the rotor mounting tabs have apertures or through holes.

In another form, the retention ring flanges extend axially through slots defined between the plurality of rotor tabs.

Conveniently, the retention ring is radially yieldable by either compression or expansion, and can be an inner retention ring or an outer retention ring.

In some forms the retention ring can a continuous spiral ring having substantially flat or planar axial faces and an inner wave spring portion, or an inner wave spring ring portion sandwiched between two substantially flat or planar rings, or a split ring, or a multi-turn spiral ring having substantially flat or planar axial faces and overlapping terminal ends, or the retention ring includes an axially compressible material sandwiched between and optionally bonded to two substantially flat or planar rings, such as wherein the compressible material is one of a wire mesh spring washer or a Belleville spring.

In another form, the hub can include a package bearing.

Advantageously, each of said rotor mounting tabs has a retention ring flange.

Additionally presented is a method of uniformly transferring braking forces from a rotor of a brake assembly about a hub of the brake assembly, the method comprising locating a plurality of mounting tabs about a mounting flange on the hub, and establishing slots about the mounting flange between adjacent pairs of the mounting tabs; locating a plurality of rotor tabs along an annular inner edge portion of the rotor; establishing a floating connection between the rotor and the mounting flange by locating each of the rotor tabs in each of the slots established between mounting tabs; and retaining the rotor tabs in the slots by engaging a retention ring with retention ring flanges provided on at least some of the mounting tabs.

In another form, the method is such that a moment arm created by axial displacement of the rotor from wheel mounting means at an end of the hub is minimized, such that torque transfer upon braking is primarily in-plane, and bending stresses within the disc brake assembly are minimized.

In another form, the method is such that the rotor floats relative to the hub to accommodate thermal expansion of the rotor tabs upon braking.

Additionally presented is a kit of parts for mounting a disc brake rotor to a brake hub having a cylindrical axial body with axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, said kit comprising a disc brake rotor comprising an inner annular aperture and a plurality of rotor tabs spaced about the inner annular aperture, the rotor tabs structured and arranged to fit into the slots on the rotor mounting flange; and at least one retention ring for securing the rotor tabs between the rotor mounting tabs and the rotor mounting flange, the retention ring structured and arranged to fit within the retention ring flanges of the plurality of rotor mounting tabs.

BRIEF DESCRIPTION OF THE DRAWINGS

The present disclosure is susceptible to various modifications and alternative forms, specific exemplary implementations thereof have been shown in the drawings and are herein described in detail. It should be understood, however, that the description herein of specific exemplary implementations is not intended to limit the disclosure to the particular forms disclosed herein. This disclosure is to cover all modifications and equivalents as defined by the appended claims. It should also be understood that the drawings are not necessarily to scale, emphasis instead being placed upon clearly illustrating principles of exemplary embodiments of the present invention. Moreover, certain dimensions may be exaggerated to help visually convey such principles. Further where considered appropriate, reference numerals may be repeated among the drawings to indicate corresponding or analogous elements. Moreover, two or more blocks or elements depicted as distinct or separate in the drawings may be combined into a single functional block or element. Similarly, a single block or element illustrated in the drawings may be implemented as multiple steps or by multiple elements in cooperation. The forms disclosed herein are illustrated by way of example, and not by way of limitation, in the figures of the accompanying drawings and in which like reference numerals refer to similar elements and in which:

FIGS. 7A-7G show various conformations of retention rings useful with the present disclosure.

DETAILED DESCRIPTION

Terminology

Figure 1:
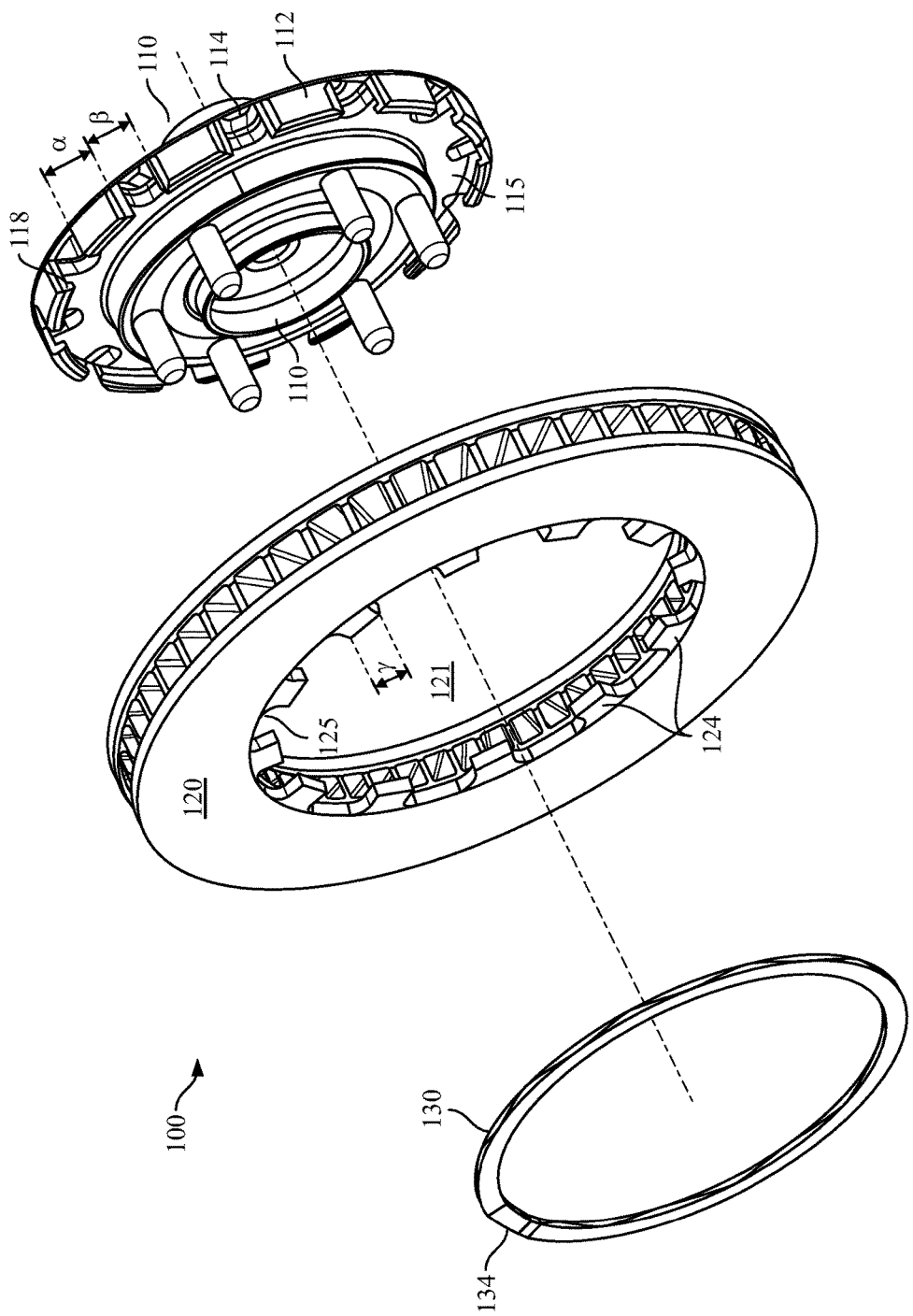
FIG. 1 is an exploded plan view of the floating disc brake assembly according to the present disclosure.

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data.

Above/below: In the following description of the representative embodiments of the invention, directional terms, such as "above", "below", "upper", "lower", etc., are used for convenience in referring to the accompanying drawings. In general, "above", "upper", "upward" and similar terms refer to a direction toward the earth's surface along a wellbore, and "below", "lower", "downward" and similar terms refer to a direction away from the earth's surface along the wellbore. Continuing with the example of relative directions in a wellbore, "upper" and "lower" may also refer to relative positions along the longitudinal dimension of a wellbore rather than relative to the surface, such as in describing both vertical and horizontal wells.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements). As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Any: The adjective "any" means one, some, or all indiscriminately of whatever quantity.

At least: As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements). The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

[Based on: "Based on" does not mean "based only on", unless expressly specified otherwise. In other words, the phrase "based on" describes both "based only on," "based at least on," and "based at least in part on."

Couple: Any use of any form of the terms "connect", "engage", "couple", "attach", or any other term describing an interaction between elements is not meant to limit the interaction to direct interaction between the elements and may also include indirect interaction between the elements described.

Determining: "Determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

Embodiments (Forms): Reference throughout the specification to "one embodiment," "an embodiment," "some embodiments," "one aspect," "an aspect," "some aspects," "some implementations," "one implementation," "an implementation," or similar construction means that a particular component, feature, structure, method, or characteristic described in connection with the embodiment, aspect, or implementation is included in at least one embodiment and/or implementation of the claimed subject matter. Thus, the appearance of the phrases "in one embodiment" or "in an embodiment" or "in some embodiments" (or "aspects" or "implementations") in various places throughout the specification are not necessarily all referring to the same embodiment and/or implementation. Furthermore, the particular features, structures, methods, or characteristics may be combined in any suitable manner in one or more embodiments or implementations.

Exemplary: "Exemplary" is used exclusively herein to mean "serving as an example, instance, or illustration." Any embodiment described herein as "exemplary" is not necessarily to be construed as preferred or advantageous over other embodiments.

May: Note that the word "may" is used throughout this application in a permissive sense (i.e., having the potential to, being able to), not a mandatory sense (i.e., must).

Operatively connected and/or coupled: Operatively connected and/or coupled means directly or indirectly connected for transmitting or conducting information, force, energy, or matter.

Optimizing: The terms "optimal," "optimizing," "optimize," "optimality," "optimization" (as well as derivatives and other forms of those terms and linguistically related words and phrases), as used herein, are not intended to be limiting in the sense of requiring the present invention to find the best solution or to make the best decision. Although a mathematically optimal solution may in fact arrive at the best of all mathematically available possibilities, real-world embodiments of optimization routines, methods, models, and processes may work towards such a goal without ever actually achieving perfection. Accordingly, one of ordinary skill in the art having benefit of the present disclosure will appreciate that these terms, in the context of the scope of the present invention, are more general. The terms may describe one or more of: 1) working towards a solution which may be the best available solution, a preferred solution, or a solution that offers a specific benefit within a range of constraints; 2) continually improving; 3) refining; 4) searching for a high point or a maximum for an objective; 5) processing to reduce a penalty function; 6) seeking to maximize one or more factors in light of competing and/or cooperative interests in maximizing, minimizing, or otherwise controlling one or more other factors, etc.

Order of steps: It should also be understood that, unless clearly indicated to the contrary, in any methods claimed herein that include more than one step or act, the order of the steps or acts of the method is not necessarily limited to the order in which the steps or acts of the method are recited.

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Description

This disclosure relates to a floating disc brake assembly which is both light weight and cost effective, and can be used with any of light duty vehicles, heavy duty vehicles, trucks, buses and railway vehicles.

One difference between the rotor in accordance with this disclosure and conventional rotors is that an attachment flange, which surrounds an inner circumferential or annular aperture in the rotor, has a series of spaced, radial rotor tabs formed as solid projections, advantageously with no apertures or through holes needed for fasteners as in conventional two-piece or floating rotors. However, if desired, apertures or through holes could be provided in either the rotor tabs or the rotor mounting tabs on the hubs.

In one form the apparatus is directed to a floating disc brake assembly comprising a disc brake rotor having an inner circumferential or annular aperture, and a plurality of rotor tabs spaced about said inner circumferential or annular aperture. The rotor fits onto a hub comprising a rotor mounting flange having a plurality of rotor mounting tabs at uniformly spaced locations about the rotor mounting flange. Adjacent pairs of the rotor mounting tabs define slots between them and some or all of the rotor mounting tabs includes a retention ring flange. Further, each rotor mounting tab has a first arcuate extent and each of the intervening slots has a second arcuate extent approximately equal to said first arcuate extent of the rotor mounting tabs. The slots and the rotor tabs are mutually arranged such that the rotor tabs are received in the slots between the rotor mounting tabs. In this manner braking forces from said rotor are transferred uniformly about the hub. The rotor is held against the rotor mounting flange by a retention ring releaseably engageable with the retention ring flanges on the rotor mounting tabs, and when engaged with the retention ring flanges, the retention ring retains the rotor tabs in the slots. The rotor mounting flange also has landings extending across at least some of the slots between the rotor mounting tabs, such that when engaged with the retention ring flanges, the retention ring and the landings act to axially retain the rotor tabs in the slots. Optionally, the hub can include a package bearing.

The incorporation of the retention ring in combination with the retention ring flanges is advantageous in avoiding the necessity of drilling holes or apertures in either or both of the rotor tabs or the rotor mounting tabs for securing the rotor to the rotor mounting flange and thus to the hub. In one form the retention ring can be an essentially continuous spiral ring having flat axial faces with a wave spring between them. In this context, the ring is continuous in the sense that it has a multiple turn spiral structure, which is not interrupted by a gap in the ring. In another embodiment the retention ring can be a three-piece ring, having an inner wave spring ring portion sandwiched between two substantially flat or planar rings, each ring having a gap to provide for compression and expansion into the retention ring flanges. In another form the retention ring can be a split ring, or a multi-turn spiral ring having substantially flat or planar axial faces and overlapping terminal ends.

Another important feature is that the rotor tabs and the rotor mounting tabs are substantially coplanar, each having first and second axial surfaces which substantially align when the rotor is mounted onto the rotor mounting flange. This configuration is important in minimizing the moment arm created by axial displacement of the rotor from wheel mounting means at an end of the body of the hub, such that torque transfer upon braking is primarily in-plane, and bending stresses within the disc brake assembly are minimized. The wheel mounting means can be a circumferential series of bolts extending from the hub.

An important feature of the rotor tabs is that each tab presents a side surface which extends radially and is driven by matching side surfaces of the rotor mounting tabs. The rotor tabs and the rotor mounting tabs have conforming, radially-oriented side surfaces which are in substantially direct contact with one another when in use. Contrary to some earlier designs which utilized deformable metal plates or spacers between side surfaces of rotor tabs and rotor mounting tabs, it has been determined that precision machining of these matching side surfaces, such that they are in direct contact with each other, results in sufficient elastic deformation to substantially equalize the stresses experienced during braking. This direct contact avoids compression deformation of metal plates or spacers which can cause eccentric movement of the parts, an out of balance condition and ultimately cracking and failure of the rotor tabs and/or rotor mounting tabs. Even when machined to close tolerances, the small clearance between the surfaces permits the rotor disc to "float" to accommodate thermal expansion of the rotor tabs upon braking.

Figure 2:
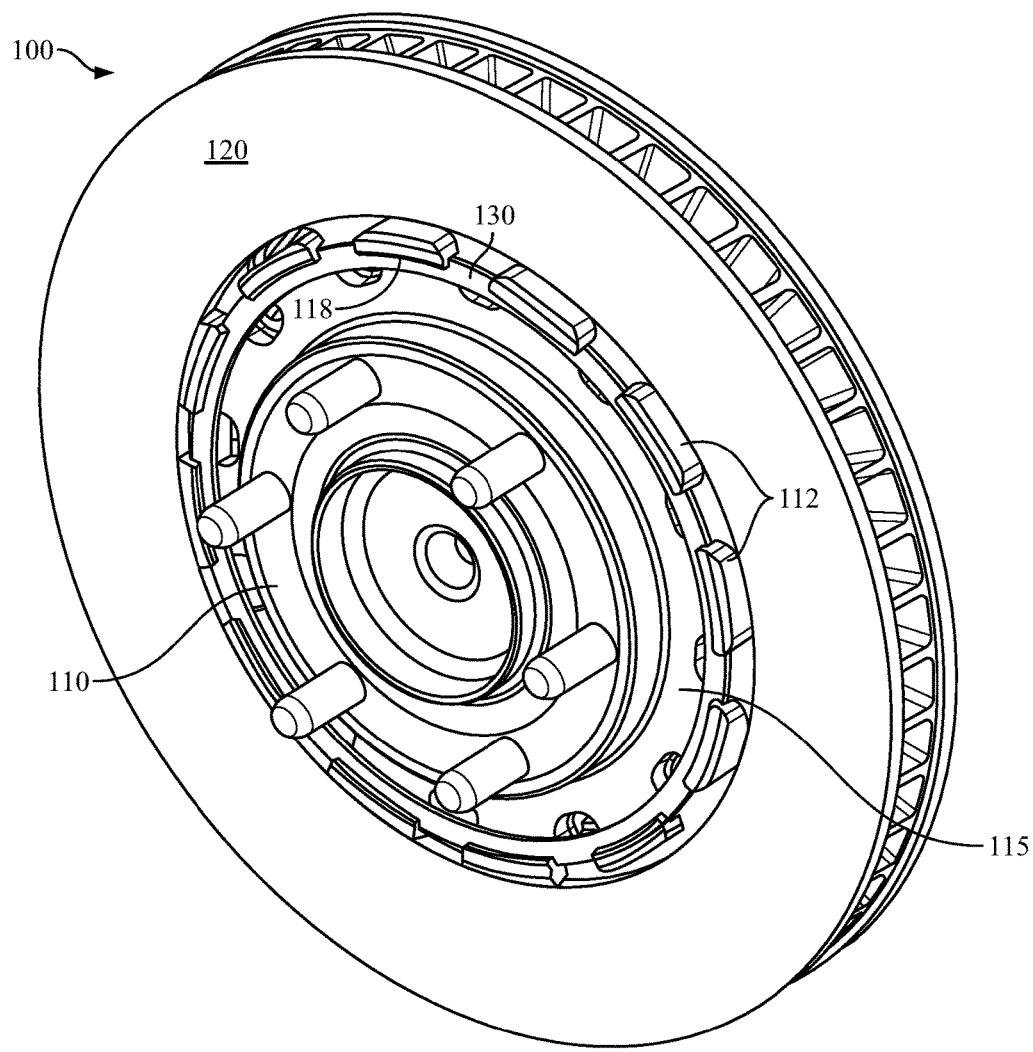
FIG. 2 is a perspective view of the front of the floating disc brake assembly of FIG. 1.
Figure 3:
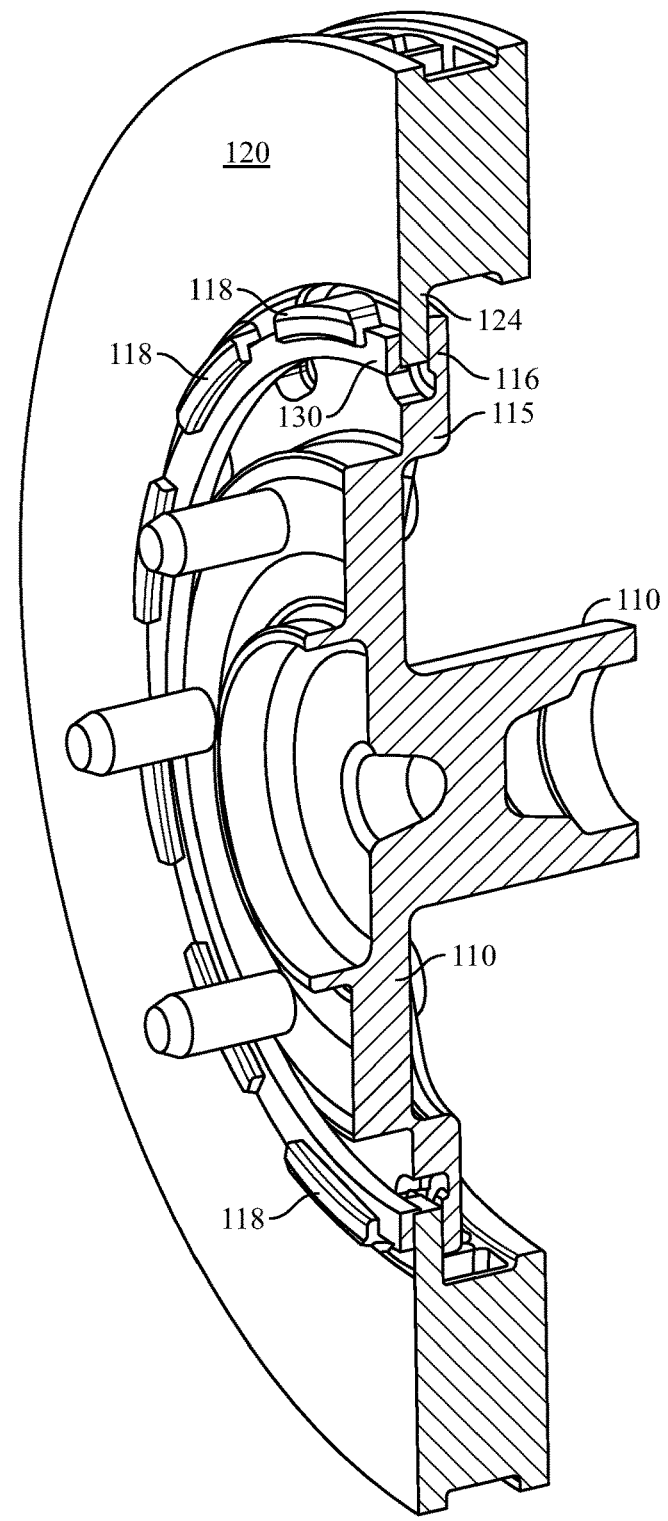
FIG. 3 is a cross-sectional view of the assembled disc brake assembly of the present disclosure.
Figure 7A:
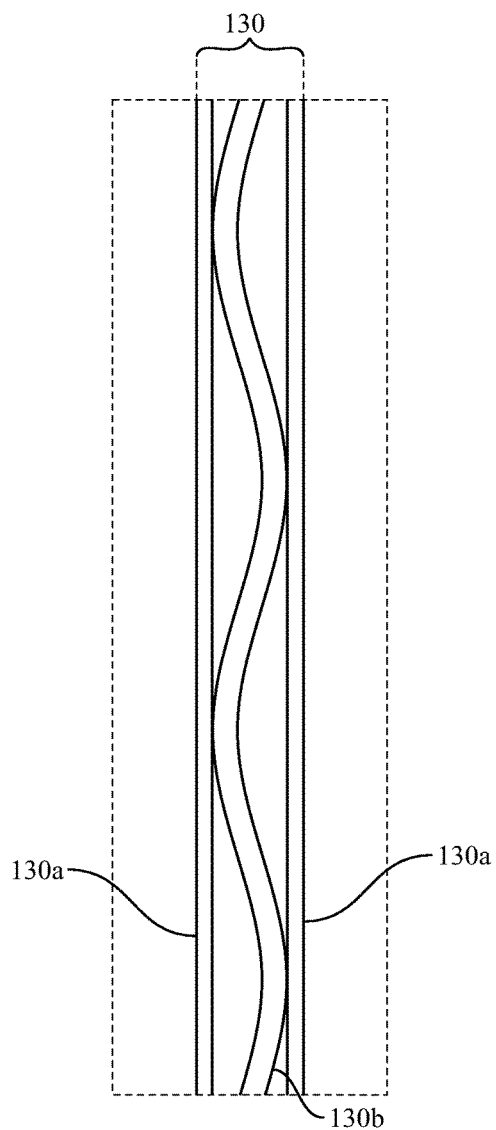

As illustrated in FIGS. 1-3, the floating disc brake assembly 100 includes a disc brake rotor 120 comprising an inner circumferential or annular aperture 121 with a plurality of rotor tabs 124 spaced about, which collectively constitute an attachment flange, a hub 110, having wheel mounting means 105 and which can include a package bearing (not shown), having a generally cylindrical axial body with axially opposed first and second ends, a rotor mounting flange 115 extending radially at or near a first end of the axial body, a plurality of rotor mounting tabs 112, each having retention ring flanges 118, the plurality of rotor mounting tabs 112 spaced about the circumference of the rotor mounting flange 115 and forming slots 114 interspersed therebetween, the slots 114 structured and arranged for receiving the rotor tabs 124, and a retention ring 130 for securing the rotor tabs 124 between the rotor mounting tabs 112 and the rotor mounting flange 115. The retention ring 130 can include a continuous spiral ring having substantially flat or planar axial faces 130a and an inner wave spring portion 130b, as shown in cross-section in FIG. 7A, and is structured and arranged to fit within the retention ring flanges 118 of the plurality of rotor mounting tabs 112, such as where the retention ring is radially yieldable and able to be compressed or expanded in its diameter to fit into the retention ring flanges 118 of the rotor mounting tabs 112.

Figure 8A:
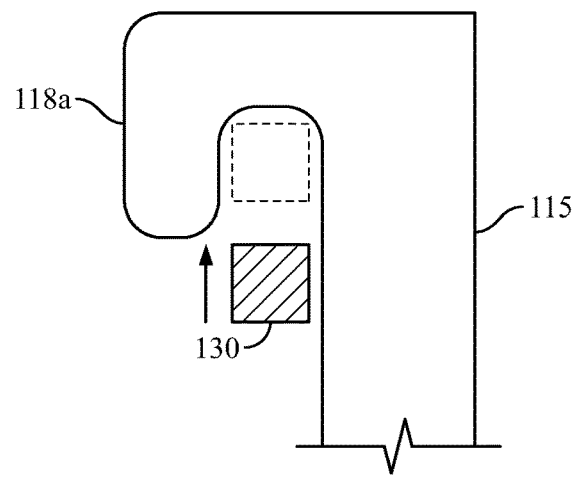
FIGS. 8A and 8B show retention ring flanges structured to receive inner and outer retention rings, respectively.
Figure 8B:
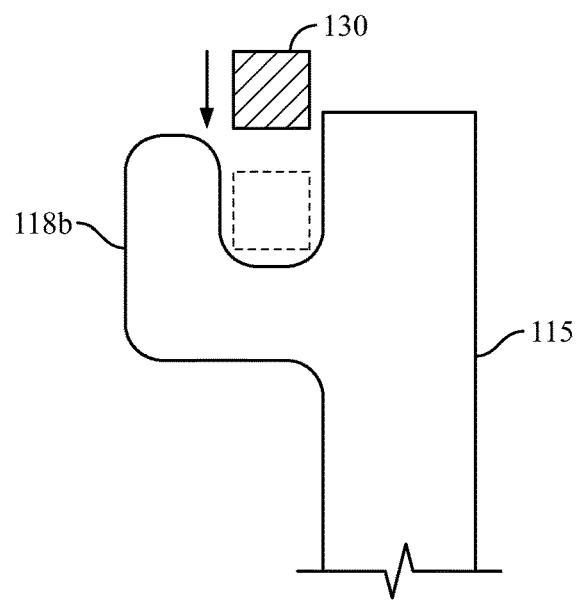

The retention ring 130 can be an inner retention ring, which is radially compressed to be placed into the retention ring flanges and then released to expand into place, or an outer retention ring, which is radially expanded to be placed into the retention ring flanges and then released to contract into place. FIG. 8A illustrates a retention ring flange 118a designed for accommodating an inner retention ring 130, and FIG. 8B illustrates a retention ring flange 118b designed for accommodating an outer retention ring 130. The arrows show the relative motions of the retention rings upon release, with the location of the rings upon release shown in phantom lines.

The inner wave spring portion 130b advantageously provides for axially biasing the planar faces outwardly, thereby securing the retention ring 130 in-place, preventing it not only from rotating around in the retention ring flanges 118, but also reducing or eliminating rattles or judder emanating from the interface between the disc brake rotor 120 and the hub 110. The continuous spiral ring 130 should be understood to have terminal ends 134 of each of the flat or planar axial faces 130a which overlap, at least to some extent.

Figure 7B:
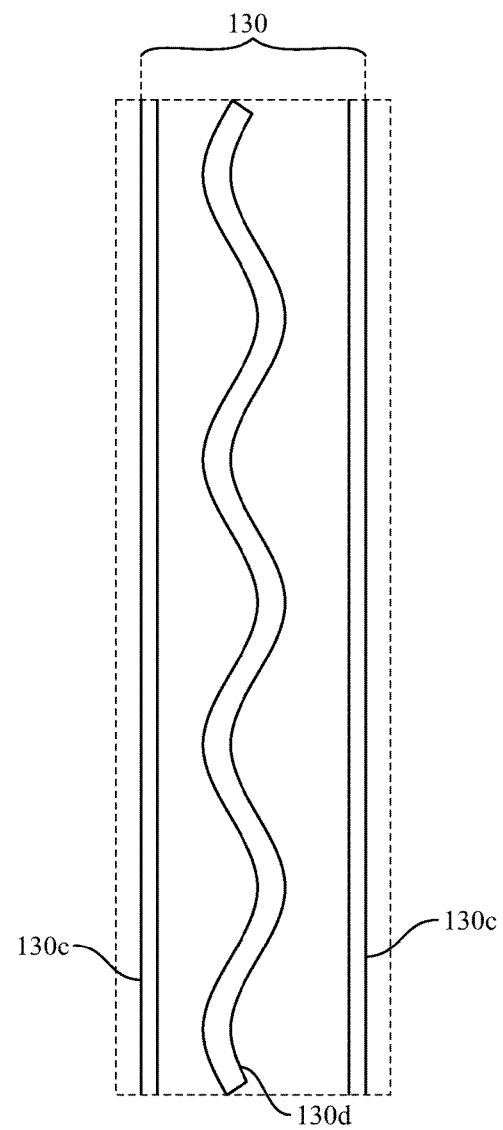
Figure 7C:
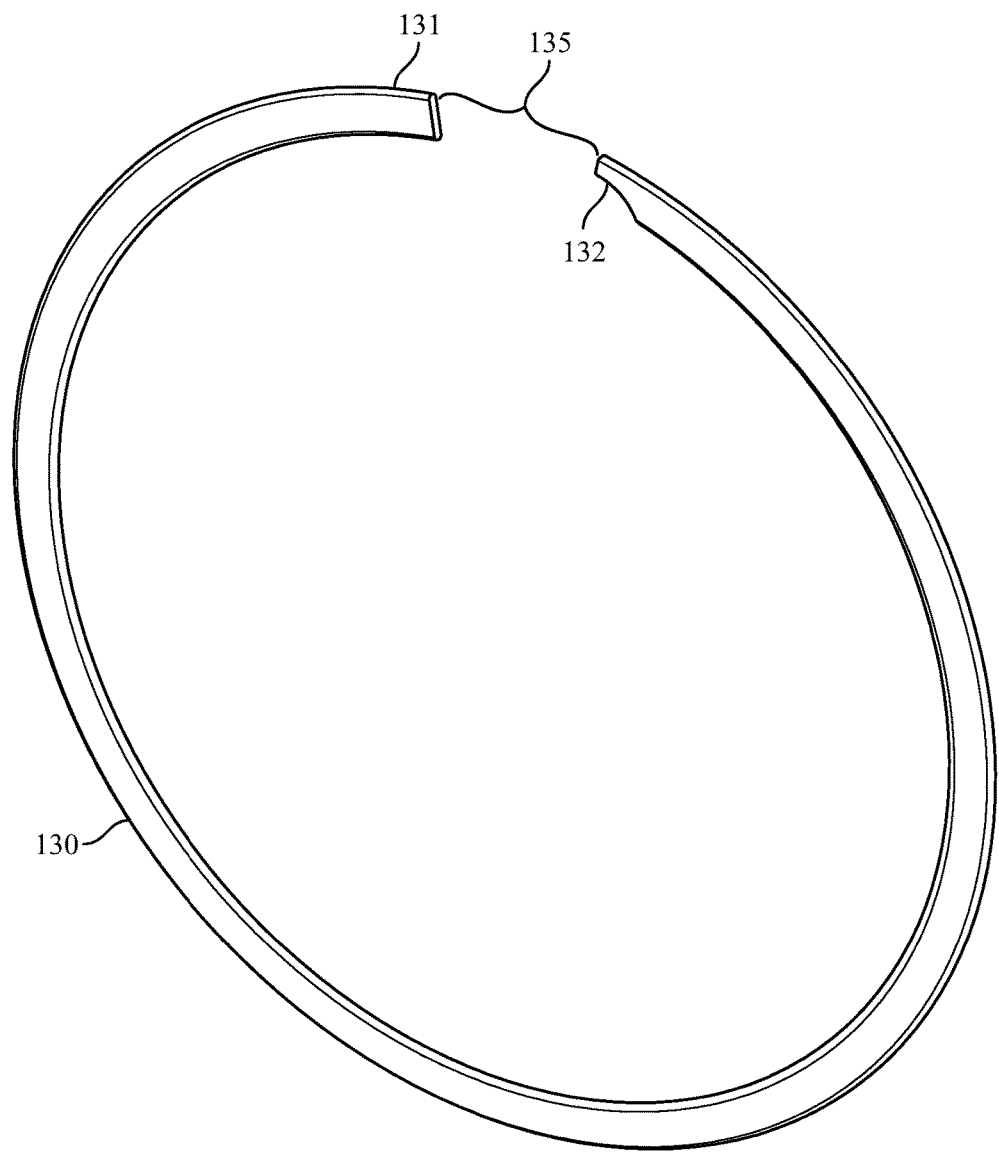
Figure 7E:
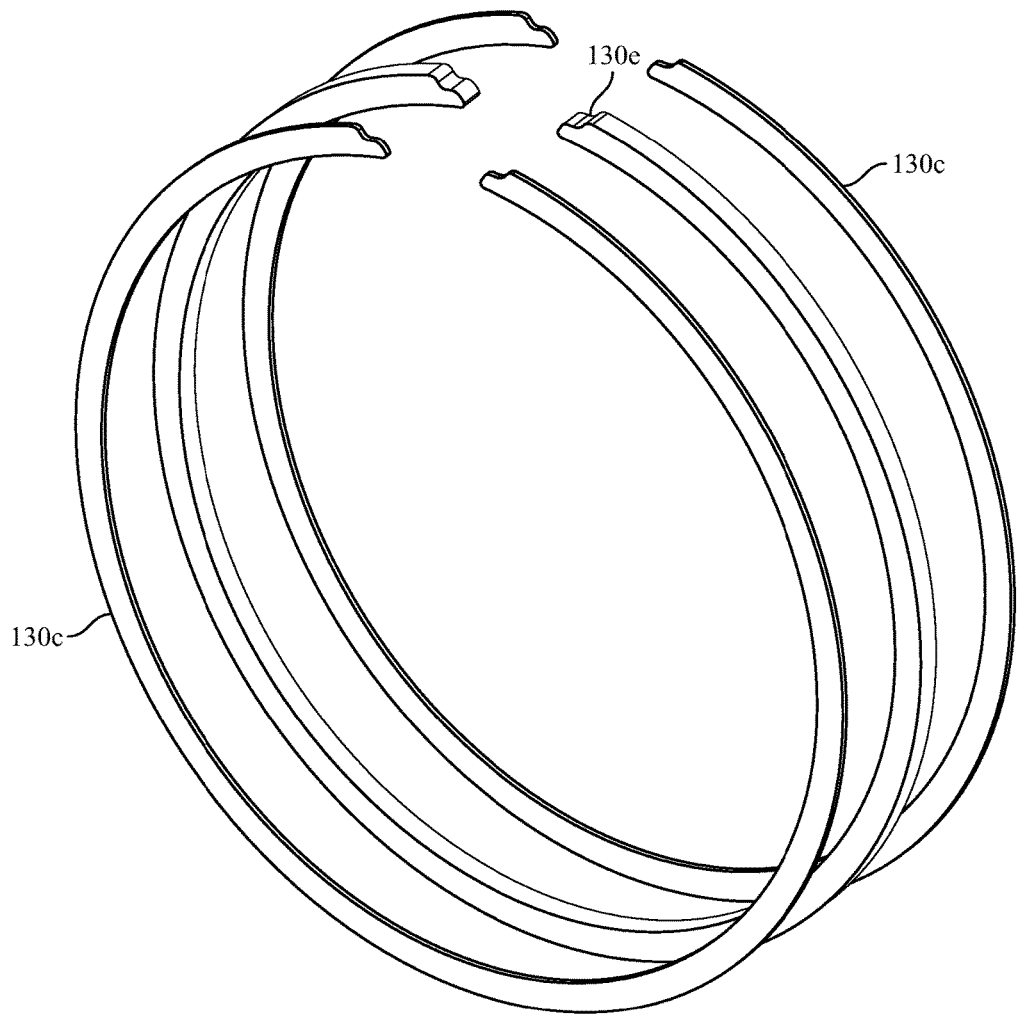
Figure 7F:
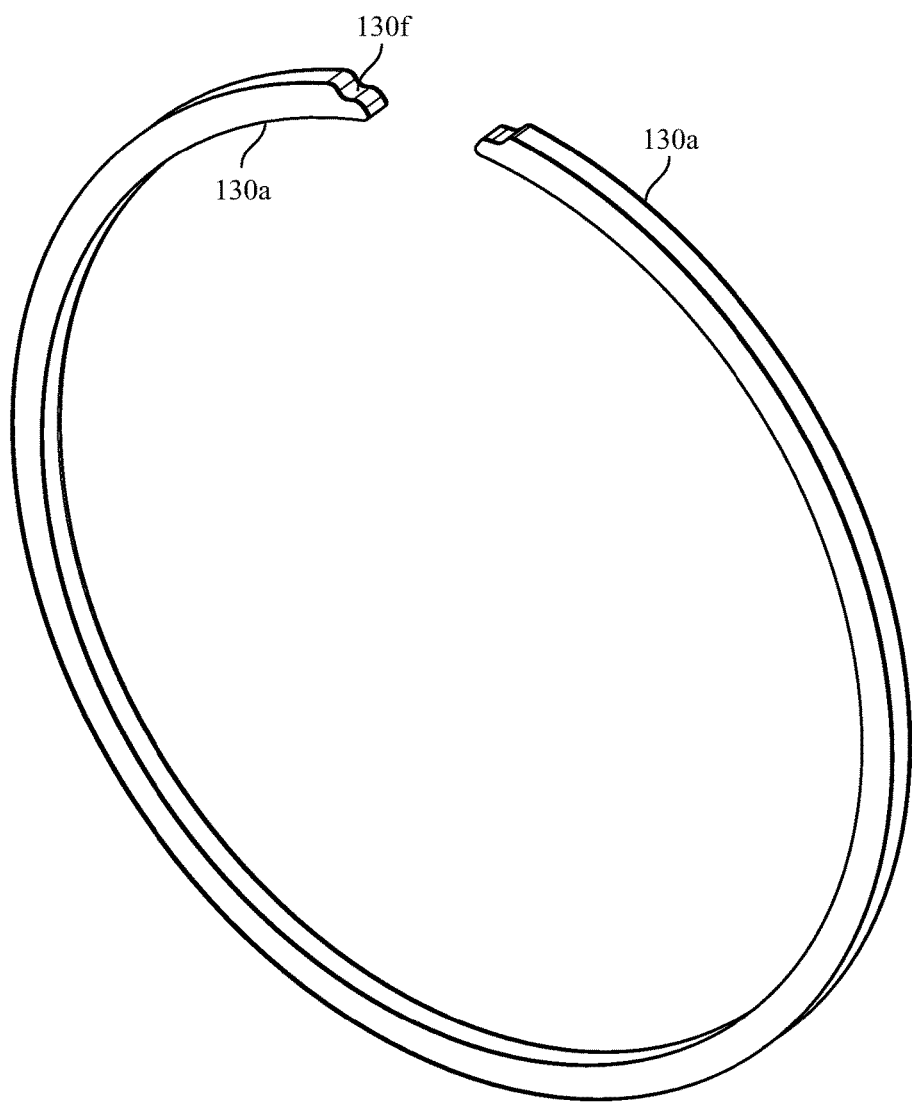
Figure 7G:
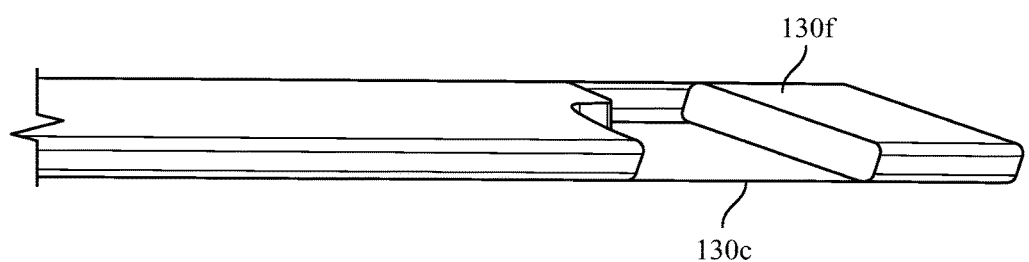

FIGS. 7B (cross-section), 7C-7F disclose alternative designs of retention rings 130 which will fit into the retention ring flanges 118 and are suitable for use to hold the rotor 120 against the hub 110. FIG. 7B illustrates a three-piece retention ring set, having an inner wave spring ring portion 130d sandwiched between two substantially flat or planar rings 130c. FIG. 7C illustrates a split ring which has terminal ends 131 and 132 having a slight gap 135 therebetween. FIG. 7D illustrates a two turn spiral ring having overlapping terminal ends 134. The amount of overlap between the terminal ends can be varied, as desired. In all forms, the retention ring 130 is radially yieldable in the direction of its diameter, such that it can be compressed or expanded to fit into the retention ring flanges 118 on the rotor mounting tabs 112 when assembling the rotor 120 to the hub 110. FIGS. 7E-7G illustrate alternative forms of the retention ring, wherein an axially compressible material is disposed between two substantially flat or planar rings. The axially compressible material can be a wire mesh spring washer 130e or 130f, which can be separate from (FIG. 7E) or bonded to (FIG. 7F) the two substantially flat or planar rings 130c, 130a. Wire mesh spring washers are available from Kinetic Structures of Phoenix, Ariz. Alternatively, the axially compressible material can be a Belleville spring 130f (FIG. 7G), which likewise can either be separate from or bonded to the two substantially flat or planar rings 130c, 130a on either axial side thereof. Similar to the inner wave spring portion 130b, the compressible material advantageously provides for axially biasing the planar faces outwardly, thereby securing the retention ring 130 in-place, preventing it not only from rotating around in the retention ring flanges 118, but also reducing or eliminating rattles or judder emanating from the interface between the disc brake rotor 120 and the hub 110.

Additionally, adjacent rotor tabs 124 define rotor slots 125 between them, into which the rotor mounting tabs 112 fit when the floating brake assembly is assembled. When in-place on the rotor mounting flange 115, the rotor tabs 124 rest against landings 116, which extend radially away from the mounting flange 115, and circumferentially between at least some of, or advantageously between all of the rotor mounting tabs 112, across the intervening slots 114 between tabs. Likewise, the rotor mounting tabs 112 fit into rotor slots 125, such that the retention ring flanges 118 extend through the inner annular aperture 121 of the rotor (FIGS. 2 and 3) and axially through rotor slots 125, permitting access to the retention ring flanges 118 from the side of the rotor 120 opposite the rotor mounting flange 115. When the retention ring 130 is fitted into the retention ring flanges 118, the rotor tabs 124 are secured into place against the landings 116 of the hub 110 and retained in rotor slots 125. When the rotor 120 is mounted on the rotor mounting flange 115, the rotor tabs 124 and the rotor mounting tabs 112 are substantially coplanar. Neither of the rotor tabs 124 or the rotor mounting tabs 112 have apertures or through holes for mounting.

Advantageously, the rotor mounting tabs 112 each have a first arcuate extent $\alpha$, and the intervening slots 114 each have a second arcuate extent $\beta$, which are approximately equal. When arranged in this fashion, rotor mounting tabs 112 are spaced uniformly about the mounting flange 115, such that braking forces from the rotor 120 are transferred uniformly about the hub 110. Likewise, the rotor tabs 124 can be spaced uniformly about the rotor flange defining the inner annular aperture 121, such that each has an arcuate extent $\gamma$ approximately equal to those of the slots 114 between the rotor mounting tabs 112. Because each arcuate extent $\alpha$, $\beta$ and $\gamma$ are approximately equal, the rotor tabs 124 readily fit into slots 114 of the mounting flange 115, and rest on landings 116. Additionally the matching arcuate extents $\alpha$, $\beta$ and $\gamma$ result in close conformance between the radially-oriented side surfaces of the rotor mounting tabs 112, and the rotor tabs 124, resulting in even and in-plane distribution of braking forces.

Figure 4:
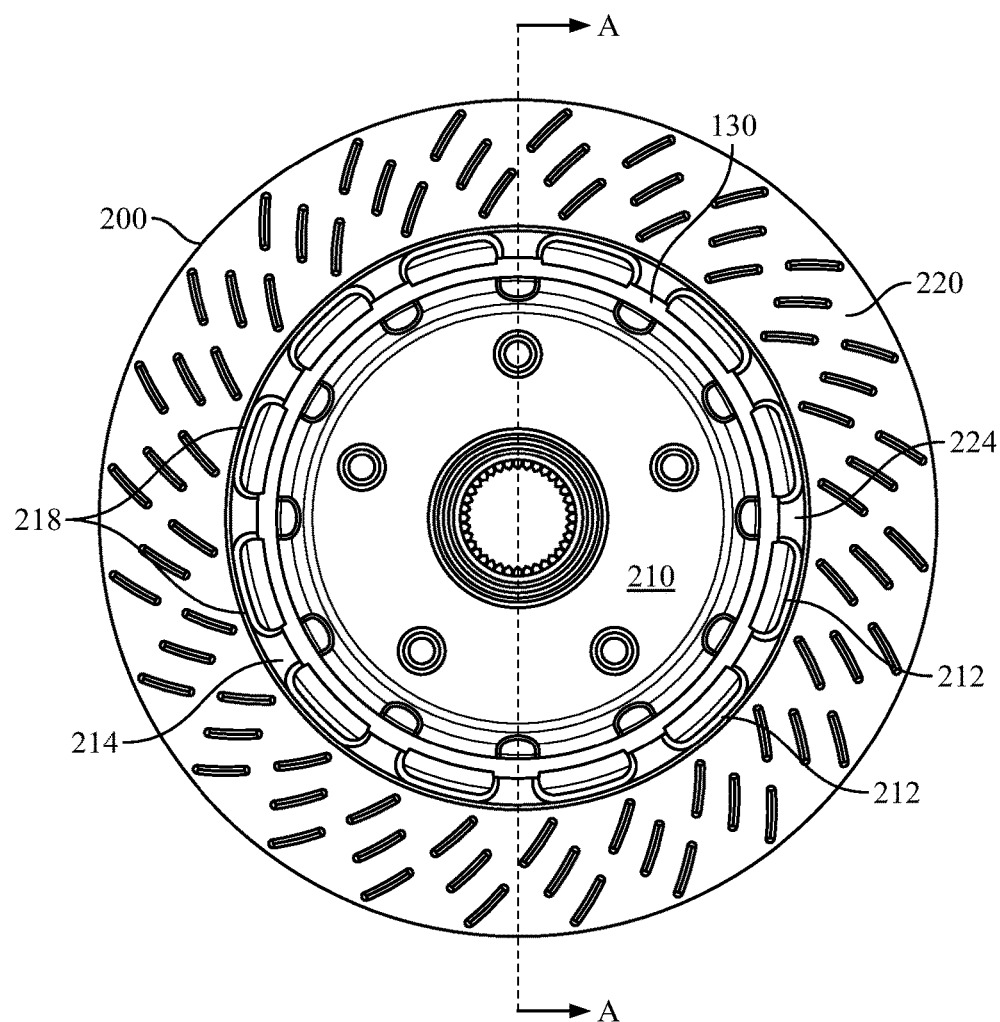
FIG. 4 is a front view of an alternative disc brake assembly according to the present disclosure.
Figure 5:
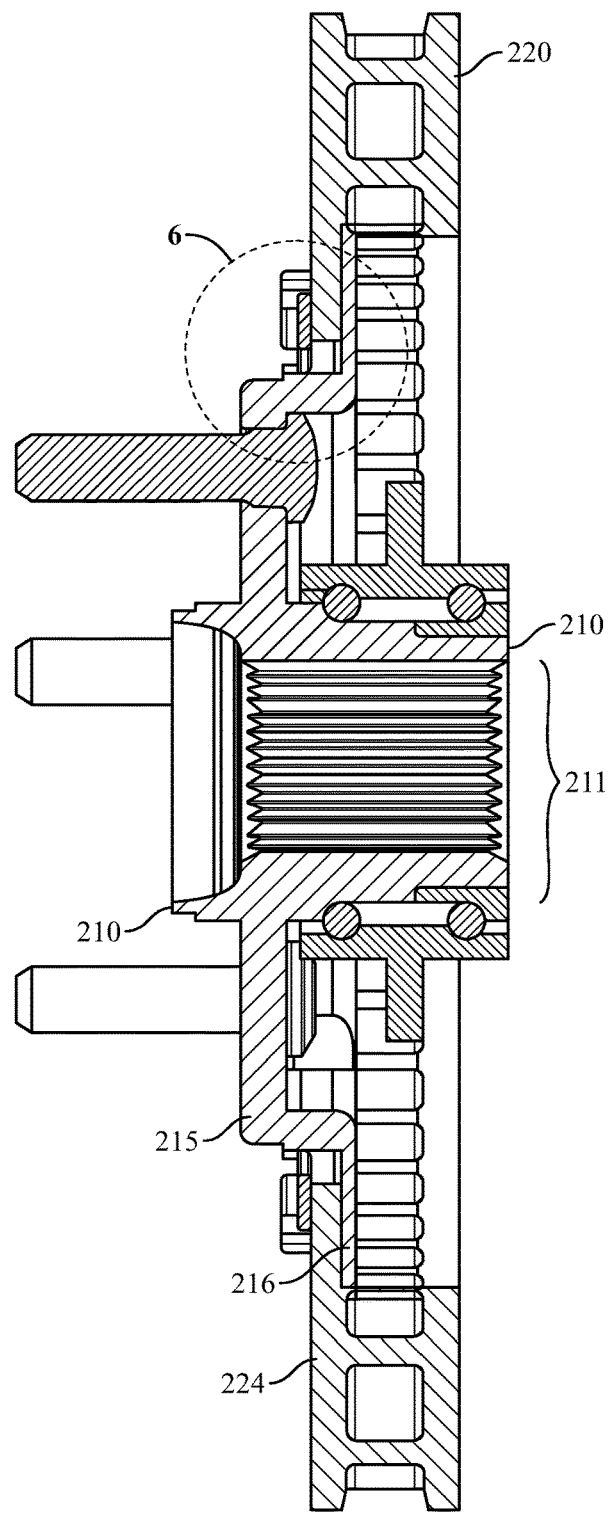
FIG. 5 is a cross-sectional view along line A-A of FIG. 4.
Figure 6:
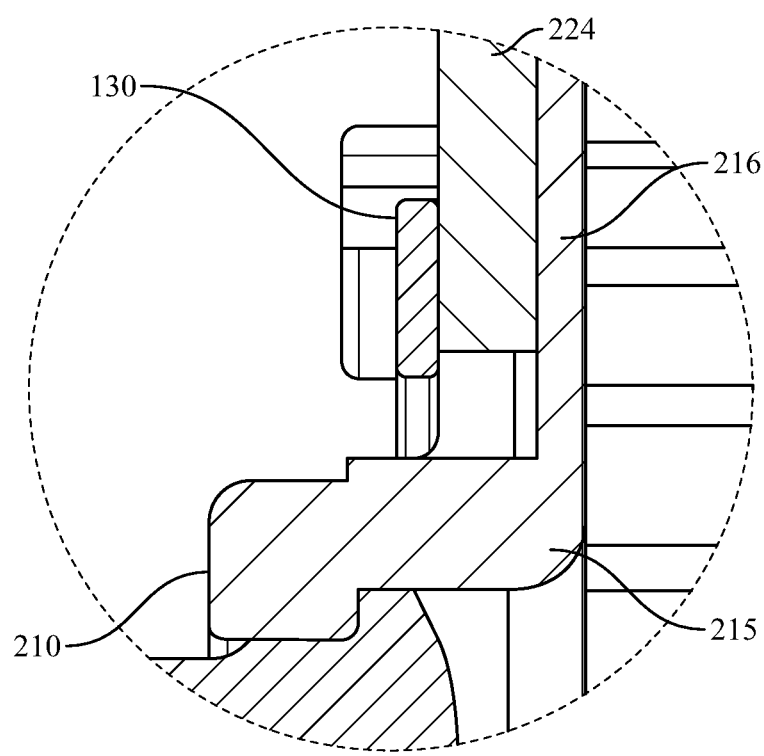
FIG. 6 is an enlarged view of the circled inset of FIG. 5.

FIGS. 4-6 illustrate an alternative form of a floating disc brake assembly 200, which includes a disc brake rotor 220 comprising an inner circumferential or annular aperture (not shown) with a plurality of rotor tabs 224 spaced about, which collectively constitute an attachment flange, a hub 210, which can include a package bearing 211, having a generally cylindrical axial body with axially opposed first and second ends, a rotor mounting flange 215 extending radially at or near a first end of the axial body, a plurality of rotor mounting tabs 212, at least some of which having retention ring flanges 218, the plurality of rotor mounting tabs 212 uniformly spaced about the rotor mounting flange 215 and forming slots 214 interspersed therebetween, the slots 214 structured and arranged for receiving the rotor tabs 224, and a retention ring 130 for securing the rotor tabs 224 between the rotor mounting tabs 212 and the rotor mounting flange 215. The retention ring 130 can include a continuous spiral ring having substantially flat or planar axial faces 130a and an inner wave spring portion 130b, as shown in cross-section in FIG. 7A, or can be any of the forms illustrated in FIGS. 7B-7F, described above, and is structured and arranged to fit within the retention ring flanges 218 of the plurality of rotor mounting tabs 212, such as where the retention ring is radially yieldable and able to be compressed or expanded in its diameter to fit into the retention ring flanges 218 of the rotor mounting tabs 212.

Another form of the disclosure is a floating disc brake assembly, comprising a disc brake rotor which includes a rotor having an inner annular aperture and a plurality of rotor tabs spaced about the inner annular aperture. The rotor is mounted to a hub having a rotor mounting flange, a plurality of rotor mounting tabs at uniformly spaced locations about the mounting flange, such that adjacent pairs of the rotor mounting tabs define slots therebetween. At least some of the rotor mounting tabs include a retention ring flange, each rotor mounting tab has a first arcuate extent and each of the slots has a second arcuate extent approximately equal to the first arcuate extent. The slots and the rotor tabs are mutually arranged such that the rotor tabs are received in the slots, whereby braking forces from the rotor are transferred uniformly about the hub. A retention ring is releaseably engageable with the retention ring flanges, and when engaged with the retention ring flanges, the retention ring retains the rotor tabs in the slots.

In another form is presented a method of uniformly transferring braking forces from a rotor of a brake assembly about a hub of the brake assembly. The method comprises uniformly locating a plurality of mounting tabs about a mounting flange on the hub, and uniformly establishing slots about the mounting flange between adjacent pairs of the mounting tabs, while maintaining a common arcuate extent for each of the mounting tabs and each of the slots. A plurality of rotor tabs are located uniformly along an annular inner edge portion of the rotor, consistently with the common arcuate extent of the mounting tabs and the slots, thus establishing a floating connection between the rotor and the mounting flange by locating each of the rotor tabs in each of the slots established between mounting tabs. The rotor tabs are retained in the slots by engaging a retention ring with retention ring flanges provided on at least some of the mounting tabs.

In another form is disclosed a kit of parts for mounting a disc brake rotor to a brake hub having a cylindrical axial body with axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, said kit comprising a disc brake rotor comprising an inner annular aperture and a plurality of rotor tabs spaced uniformly about the inner annular aperture, the rotor tabs structured and arranged to fit into the slots on the rotor mounting flange; and at least one retention ring for securing the rotor tabs between the rotor mounting tabs and the rotor mounting flange, the retention ring structured and arranged to fit within the retention ring flanges of the plurality of rotor mounting tabs.

The kit, including the rotor and the retention ring, is useful for replacing worn rotors on hubs previously mounted on a vehicle.

Further illustrative, non-exclusive examples of assemblies and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT1. A floating disc brake assembly, comprising a disc brake rotor comprising an inner circumferential aperture having a plurality of rotor tabs spaced about the aperture; a hub comprising a cylindrical axial body having axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, the slots structured and arranged for receiving the rotor tabs; and at least one retention ring for securing the rotor tabs between the rotor mounting tabs and the rotor mounting flange, the retention ring structured and arranged to fit within the retention ring flanges of the plurality of rotor mounting tabs.

PCT2. The floating disc brake assembly of paragraph PCT1, further comprising landings extending across at least some of said slots between said rotor mounting tabs, such that when engaged with said retention ring flanges, said retention ring and said landings axially retain said rotor tabs in said slots.

PCT3. The floating disc brake assembly of either one of paragraphs PCT1 or paragraph PCT2, wherein the rotor tabs and the rotor mounting tabs are substantially coplanar when the rotor is mounted on the hub.

PCT4. The floating disc brake assembly of any one of paragraphs PCT1 to paragraph PCT3, wherein neither the rotor tabs nor the rotor mounting tabs have apertures or through holes.

PCT5. The floating disc brake assembly of any one of paragraphs PCT1 to paragraph PCT4, wherein the retention ring flanges extend axially through slots formed between the plurality of rotor tabs.

PCT6. The floating disc brake assembly of any one of paragraphs PCT1 to paragraph PCT5, wherein the retention ring is radially yieldable by either compression or expansion, and can be an inner retention ring or an outer retention ring.

PCT7. The floating disc brake assembly of any one of paragraphs PCT1 to paragraph PCT6, wherein the retention ring can be in the form of a continuous spiral ring having substantially flat or planar axial faces and an inner wave spring portion, or an inner wave spring ring portion sandwiched between two substantially flat or planar rings, or a split ring, or a multi-turn spiral ring having substantially flat or planar axial faces and overlapping terminal ends, or wherein the retention ring includes an axially compressible material sandwiched between and optionally bonded to two substantially flat or planar rings, such as wherein the compressible material is one of a wire mesh spring washer or a Belleville spring.

PCT8. The floating disc brake assembly of any one of paragraphs PCT1 to paragraph PCT7, wherein the hub includes a package bearing.

PCT9. The floating disc brake assembly of any one of paragraphs PCT1 to paragraph PCT8, wherein each of said rotor mounting tabs has a retention ring.

PCT10. A method of uniformly transferring braking forces from a rotor of a brake assembly about a hub of the brake assembly, the method comprising locating a plurality of mounting tabs about a mounting flange on the hub, and establishing slots about the mounting flange between adjacent pairs of the mounting; locating a plurality of rotor tabs along an annular inner edge portion of the rotor; establishing a floating connection between the rotor and the mounting flange by locating each of the rotor tabs in each of the slots established between mounting tabs; and retaining the rotor tabs in the slots by engaging a retention ring with retention ring flanges provided on at least some of the mounting tabs.

PCT11. The method of paragraph PCT10, wherein a moment arm created by axial displacement of the rotor from wheel mounting means at an end of the hub is minimized, such that torque transfer upon braking is primarily in-plane, and bending stresses within the disc brake assembly are minimized.

PCT12. The method of either paragraph PCT10 or paragraph PCT11, wherein the rotor floats relative to the hub to accommodate thermal expansion of the rotor tabs upon braking.

PCT13. A kit of parts for mounting a disc brake rotor to a brake hub having a cylindrical axial body with axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, said kit comprising a disc brake rotor comprising an inner annular aperture and a plurality of rotor tabs spaced about the inner annular aperture, the rotor tabs structured and arranged to fit into the slots on the rotor mounting flange; and at least one retention ring for securing the rotor tabs between the rotor mounting tabs and the rotor mounting flange, the retention ring structured and arranged to fit within the retention ring flanges of the plurality of rotor mounting tabs.

INDUSTRIAL APPLICABILITY

The apparatus and methods disclosed herein are applicable to the automotive industry.

It is believed that the disclosure set forth above encompasses multiple distinct embodiments with independent utility. While each of these embodiments has been disclosed in its preferred form, the specific embodiments thereof as disclosed and illustrated herein are not to be considered in a limiting sense as numerous variations are possible. The subject matter of the embodiments includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed embodiments and are novel and non-obvious. Embodiments of other combinations and subcombinations of features, functions, elements and/or properties may be claimed through amendment of the present claims or presentation of new claims in this or a related application. Such amended or new claims, whether they are directed to a different embodiment or directed to the same embodiment, whether different, broader, narrower, or equal in scope to the original claims, are also regarded as included within the subject matter of the present disclosure.

While the present disclosure has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present disclosure.

The invention claimed is:

1. A floating disc brake assembly, comprising:
   a disc brake rotor comprising an inner circumferential aperture having a plurality of rotor tabs spaced about the aperture;
   a hub comprising a cylindrical axial body having axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, the slots structured and arranged for receiving the rotor tabs;
   at least one retention ring for securing the rotor tabs between the rotor mounting tabs and the rotor mounting flange, the retention ring structured and arranged to fit within the retention ring flanges of the plurality of rotor mounting tabs, and wherein the retention ring is a multi-turn spiral ring having substantially flat or planar axial faces, overlapping terminal ends and an axially compressible material sandwiched between the flat or planar axial faces.

2. The floating disc brake assembly of claim 1, further comprising landings extending across at least some of said slots between said rotor mounting tabs, such that when engaged with said retention ring flanges, said retention ring and said landings axially retain said rotor tabs in said slots.

3. The floating disc brake assembly of claim 1, wherein the rotor tabs and the rotor mounting tabs are substantially coplanar when the rotor is mounted on the hub.

4. The floating disc brake assembly of claim 1, wherein neither the rotor tabs nor the rotor mounting tabs have apertures or through holes.

5. The floating disc brake assembly of claim 1, wherein the retention ring flanges extend axially through slots defined between the plurality of rotor tabs.

6. The floating disc brake assembly of claim 1, wherein said retention ring is radially yieldable by either compression or expansion, and can be an inner retention ring or an outer retention ring.

7. The floating disc brake assembly of claim 1, wherein the axially compressible material is a wave spring.

8. The floating disc brake assembly of claim 1, wherein the axially compressible material is one of a wire mesh spring washer or a Belleville spring.

9. The floating disc brake assembly of claim 1, wherein the hub includes a package bearing.

10. The floating disc brake assembly of claim 1, wherein each of said rotor mounting tabs has a retention ring flange.

11. A method of uniformly transferring braking forces from a rotor of a brake assembly about a hub of the brake assembly, said method comprising:

locating a plurality of mounting tabs about a mounting flange on said hub, and establishing slots about said mounting flange between adjacent pairs of said mounting tabs;

locating a plurality of rotor tabs along an annular inner edge portion of said rotor;

establishing a floating connection between said rotor and said mounting flange by locating each of said rotor tabs in each of said slots established between mounting tabs; and retaining said rotor tabs in said slots by engaging a retention ring with retention ring flanges provided on at least some of said mounting tabs, wherein the retention ring is a multi-turn spiral ring having substantially flat or planar axial faces, overlapping terminal ends and an axially compressible material sandwiched between the flat or planar axial faces.

12. The method of claim 11, wherein the rotor floats relative to the hub to accommodate thermal expansion of the rotor tabs upon braking.

13. A kit of parts for mounting a disc brake rotor to a brake hub having a cylindrical axial body with axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, said kit comprising:

a disc brake rotor comprising an inner annular aperture and a plurality of rotor tabs spaced uniformly about the inner annular aperture, the rotor tabs structured and arranged to fit into the slots on the rotor mounting flange; and at least one retention ring for securing the rotor tabs between the rotor mounting tabs and the rotor mounting flange, the retention ring structured and arranged to fit within the retention ring flanges of the plurality of rotor mounting tabs, and wherein the retention ring is a multi-turn spiral ring having substantially flat or planar axial faces, overlapping terminal ends and an axially compressible material sandwiched between the flat or planar axial faces.

14. A floating disc brake assembly, comprising:

a disc brake rotor comprising an inner circumferential aperture having a plurality of rotor tabs spaced about the aperture;

a hub comprising a cylindrical axial body having axially opposed first and second ends, a rotor mounting flange extending radially at or near the first end of the axial body, a plurality of rotor mounting tabs, at least some of which having retention ring flanges, the plurality of rotor mounting tabs spaced about the rotor mounting flange and forming slots interspersed therebetween, the slots structured and arranged for receiving the rotor tabs;

at least one retention ring for securing the rotor tabs between the rotor mounting tabs and the rotor mounting flange, the retention ring structured and arranged to fit within the retention ring flanges of the plurality of rotor mounting tabs, and wherein the retention ring is a multi-turn spiral ring and includes an inner wave spring ring portion sandwiched between two substantially flat or planar faces of the multi-turn spiral ring.

* * * * *